(12) United States Patent
Lin et al.

(10) Patent No.: US 8,160,335 B2
(45) Date of Patent: *Apr. 17, 2012

(54) COMPUTER AIDED DIAGNOSIS USING DERIVED IMAGES

(75) Inventors: Jyh-Shyan Lin, North Potomac, MD (US); Ruiping Li, Rockville, MD (US); Fleming Lure, Potomac, MD (US); Edward A. Martello, Glenwood, MD (US); Tong Wei, Clarksburg, MD (US); Rujirutana Sriikanchana, Columbia, MD (US); Hui Zhao, Silver Spring, MD (US); Xin-Wei Xu, Gaithersburg, MD (US)

(73) Assignee: Riverain Medical Group, LLC, Miamisburg, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/042,748

(22) Filed: Mar. 8, 2011
(Under 37 CFR 1.47)

(65) Prior Publication Data
US 2011/0164802 A1    Jul. 7, 2011

Related U.S. Application Data

(63) Continuation of application No. 11/850,868, filed on Sep. 6, 2007, now Pat. No. 7,903,855, which is a continuation of application No. 11/561,927, filed on Nov. 21, 2006, now abandoned.

(60) Provisional application No. 60/738,977, filed on Nov. 23, 2005.

(51) Int. Cl.
*G06K 9/00* (2006.01)
*G01N 23/06* (2006.01)
(52) U.S. Cl. ........................ 382/128; 382/275; 378/56
(58) Field of Classification Search .................. 382/100, 382/128, 129, 130, 131, 132, 133, 134, 155, 382/156, 168, 181, 224, 232, 254, 255, 260, 382/274, 275, 276, 305, 312; 378/4, 21, 378/56; 706/2; 713/171
See application file for complete search history.

(56) References Cited

U.S. PATENT DOCUMENTS

| | | | | |
|---|---|---|---|---|
| 6,438,201 | B1 * | 8/2002 | Mazess et al. | 378/56 |
| 6,549,646 | B1 * | 4/2003 | Yeh et al. | 382/132 |
| 6,654,728 | B1 * | 11/2003 | Li et al. | 706/2 |
| 6,760,468 | B1 * | 7/2004 | Yeh et al. | 382/132 |
| 6,795,521 | B2 * | 9/2004 | Hsu et al. | 378/4 |
| 2005/0027985 | A1 * | 2/2005 | Sprunk et al. | 713/171 |

OTHER PUBLICATIONS

Written Opinion and International Search Report issued in corresponding International Application No. PCT/US06/61205 on Mar. 31, 2008.
Notification Concerning Transmittal of International Preliminary Report on Patentability (with IPRP) issued in related International Application No. PCT/US2006/061205 on May 27, 2008.

* cited by examiner

*Primary Examiner* — Seyed Azarian
(74) *Attorney, Agent, or Firm* — Connolly Bove Lodge & Hutz LLP

(57) ABSTRACT

Computer-aided diagnosis techniques may be combined with techniques to obtain derived images from radiographic images to provide enhanced computer-aided diagnosis of, for example, lung nodules.

15 Claims, 4 Drawing Sheets

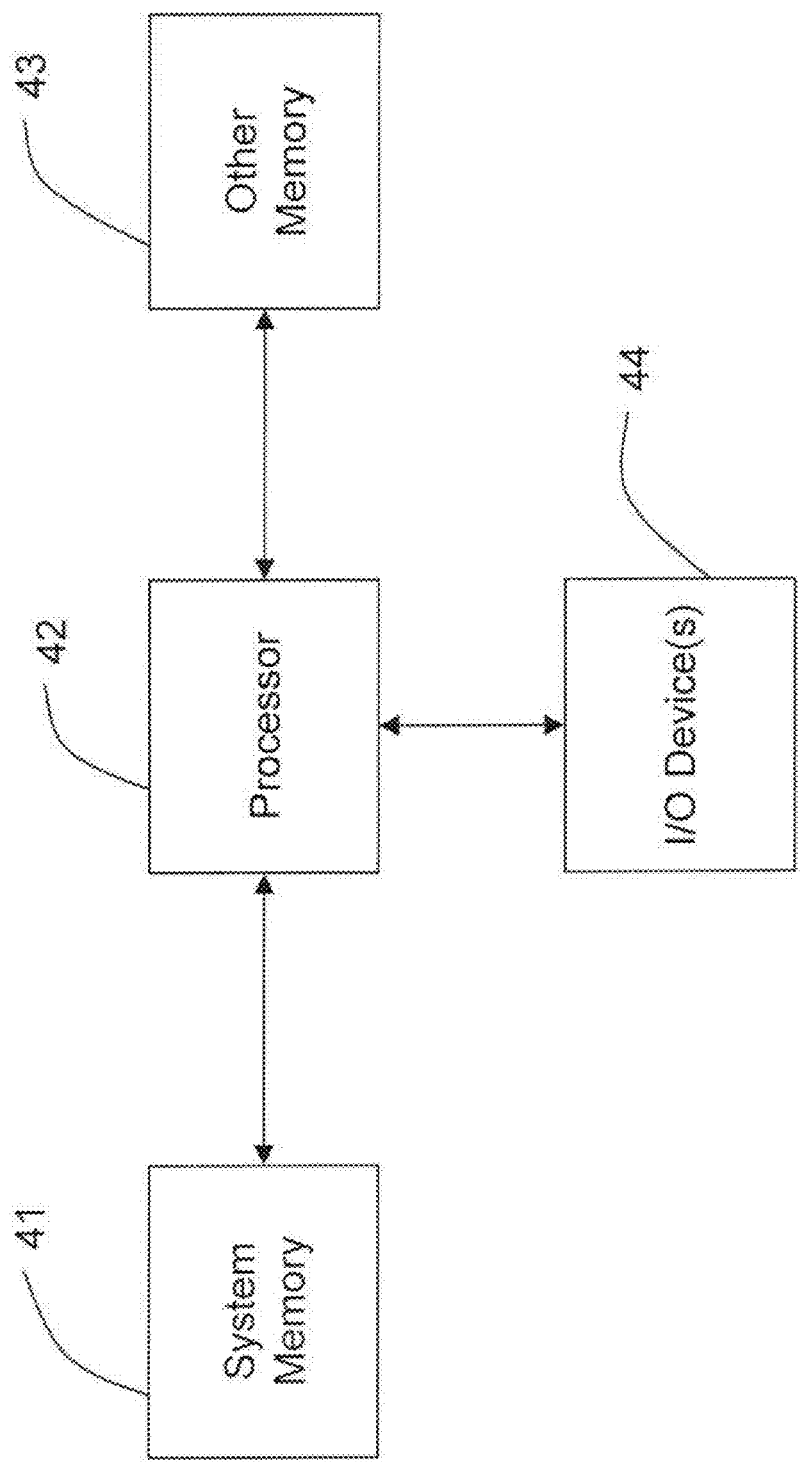

COMPUTER AIDED DIAGNOSIS USING DERIVED IMAGES

CROSS-REFERENCE TO RELATED APPLICATIONS

The present application is a continuation of U.S. application Ser. No. 11/850,868, filed on Sep. 6, 2007, which is a continuation of U.S. application Ser. No. 11/561,927, filed on Nov. 21, 2006, which draws priority from U.S. Provisional Application No. 60/738,977, filed Nov. 23. 2005 all commonly-assigned and incorporated by reference herein in its entirety.

FIELD OF THE INVENTION

Embodiments of the present invention are directed to techniques and systems for computer-aided diagnosis.

BACKGROUND OF THE INVENTION

Dual-energy chest radiographs may be obtained either simultaneously or in rapid sequence with two x-ray exposures at different energies. Because of the non-linear nature of x-ray absorption in human body as a function of x-ray energy spectrum, dual-energy imaging techniques can he used to separate the image into two components: one primarily is composed of water (i.e., soft-tissue) and another primarily composed of calcium (i.e., bone). Due to the fact that the shadow of the ribs does not appear on the soft-tissue image, lung disease can be seen more readily on the soft-tissue image than in conventional chest x-rays.

FIG. 1 shows an example of how dual-energy radiography may be used to obtain chest images. In this example, two digital images, 11 and 12, have been acquired at different effective energy levels (here, 120 Kvp and 60 Kvp). These digital images have been supplied to a separation algorithm 13 that has, based on different x-ray absorption characteristics, produced a "standard" image 14, a bone equivalent image 15, and a soft-tissue equivalent image 16. In soft-tissue image 16, it can be seen that the shadows of the ribs and clavicles have been substantially removed.

However, dual-energy radiographs display the lungs and their structures with relatively low contrast due to higher image noise on the soft-tissue image. Consequently some nodules can appear relatively indistinct and may be easier for a radiologist to detect on images from a conventional chest radiograph. Moreover, in some cases, mis-registration of the image pair used to form the bone and soft-tissue images can result in artifacts that obscure lung nodules.

SUMMARY OF THE INVENTION

Embodiments of the present invention have, among other objects, the object of overcoming the above shortcomings. In particular, embodiments of the present invention may comprise an integrated computer-aided detection (CAD) system that can combine information from a "standard" chest radiograph, a soft-tissue radiograph, and a bone-like radiograph, and all of these may be generated from dual-energy radiography, as shown in FIG. 1.

Embodiments of the present invention may comprise methods, systems, and/or software embodied on computer-readable media.

BRIEF DESCRIPTION OF THE DRAWINGS

Various embodiments of the present invention will he understood and appreciated more fully from the following detailed description, taken in conjunction with the drawings, in which:

FIG. 4 shows a conceptual block diagram of a system in which the invention may be fully or partially embodied.

DETAILED DESCRIPTION OF VARIOUS EMBODIMENTS

Figure 1:
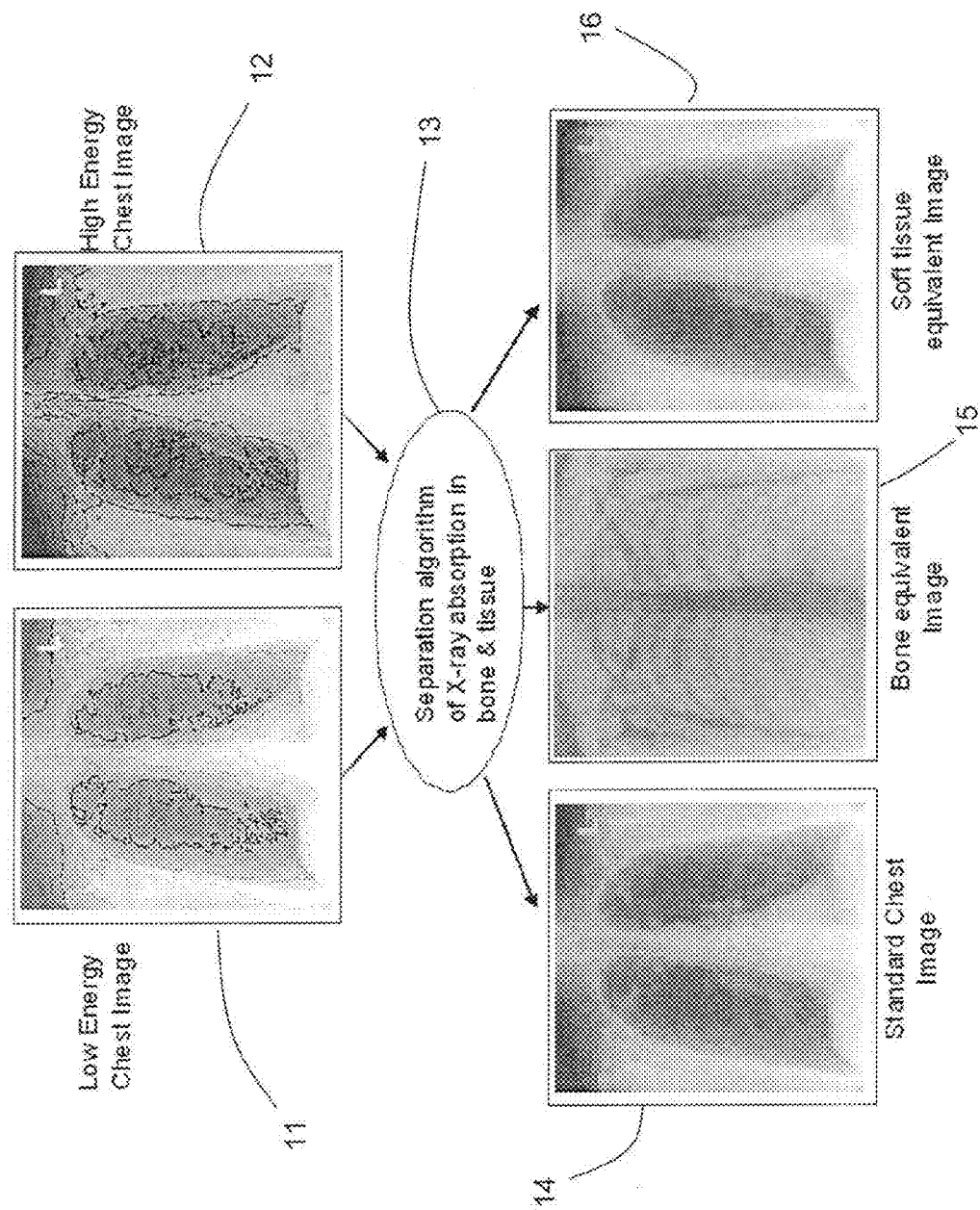
FIG. 1 shows an example of images produced from a dual-energy radiography system, prior to and after applying a separation algorithm, which may be used in various embodiments of the invention.
Figure 2:
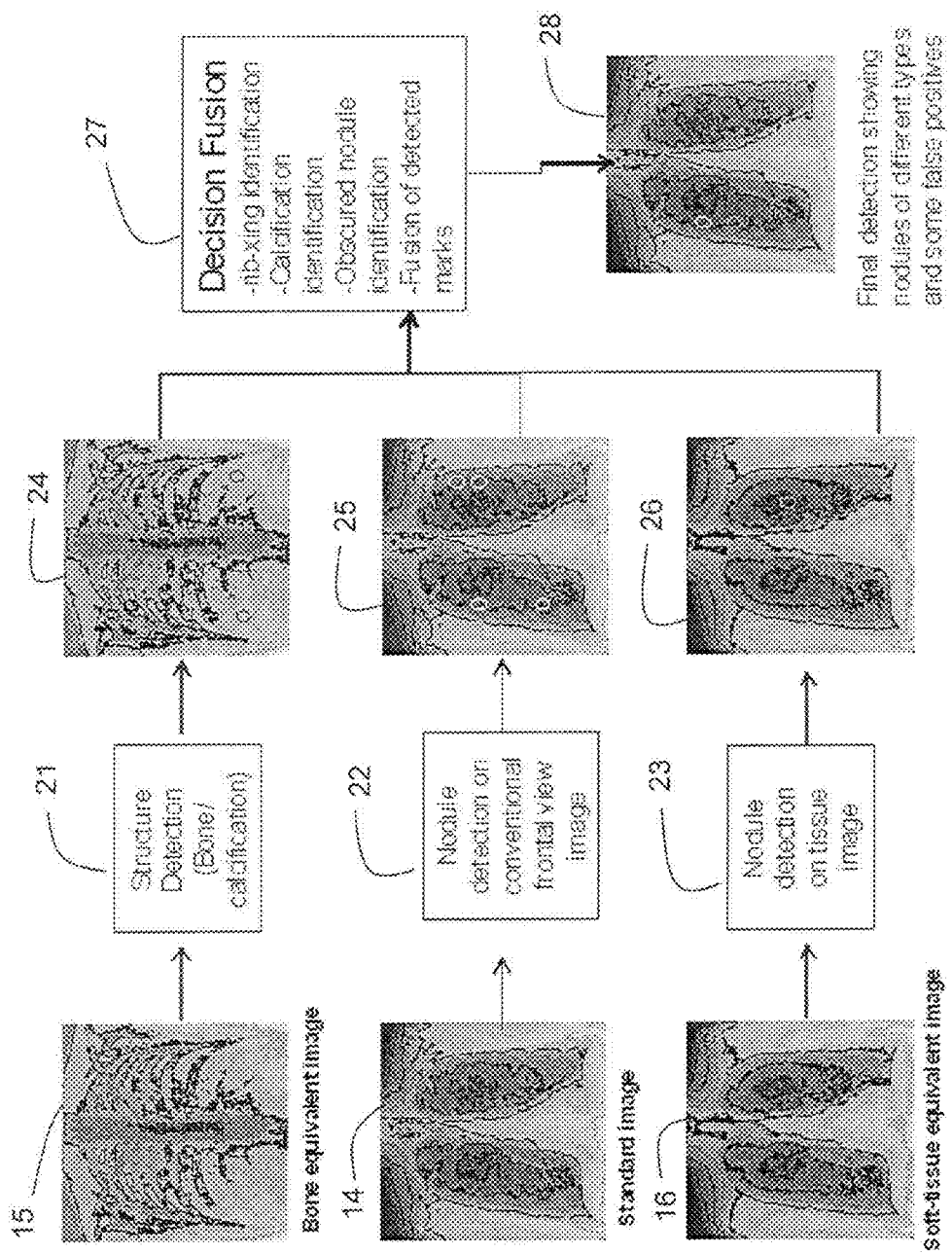
FIG. 2 shows a pictorial representation/flow diagram of a method and/or system of using images that may be produced by a method as reflected in FIG. 1 to perform detection of nodules, according to an embodiment of the invention.

FIG. 2 describes a method, according to an embodiment of the invention, in which images 14-16 produced, for example, as shown in FIG. 1, may be used in nodule detection. As shown in FIG. 2, bone equivalent image 15 may be applied to a structure detection module 21, standard image 14 may be applied to a nodule detection module 22, and soft-tissue equivalent image 16 may he applied to a nodule detection module 23. The results of these processing modules 21-23 are structure and/or nodule identifications based on the respective images 15, 14, and 16. The results may also be shown on images 24-26.

In some embodiments of the invention, the detection modules 21-23 may be implemented using parallel processing and/or processing pipelines.

To further elaborate on the images 24-26, the detection output 24 from a bone equivalent image 15 may show calcium and/or bone structures. The detection output 25 from a soft-tissue equivalent image 16 may show nodules and/or end-on (blood) vessels, which may result in finding nodules that do not appear in conventional images, and which may rarely show ribs (note, however, that it may be possible that a nodule may end up being hidden, e.g., behind the heart). The detection output 26 from a standard image 14 may show nodules, bones calcium structures, and/or (blood) vessels, and this output may sometimes reveal a nodule that may be hidden in the detection output 25.

Figure 3:
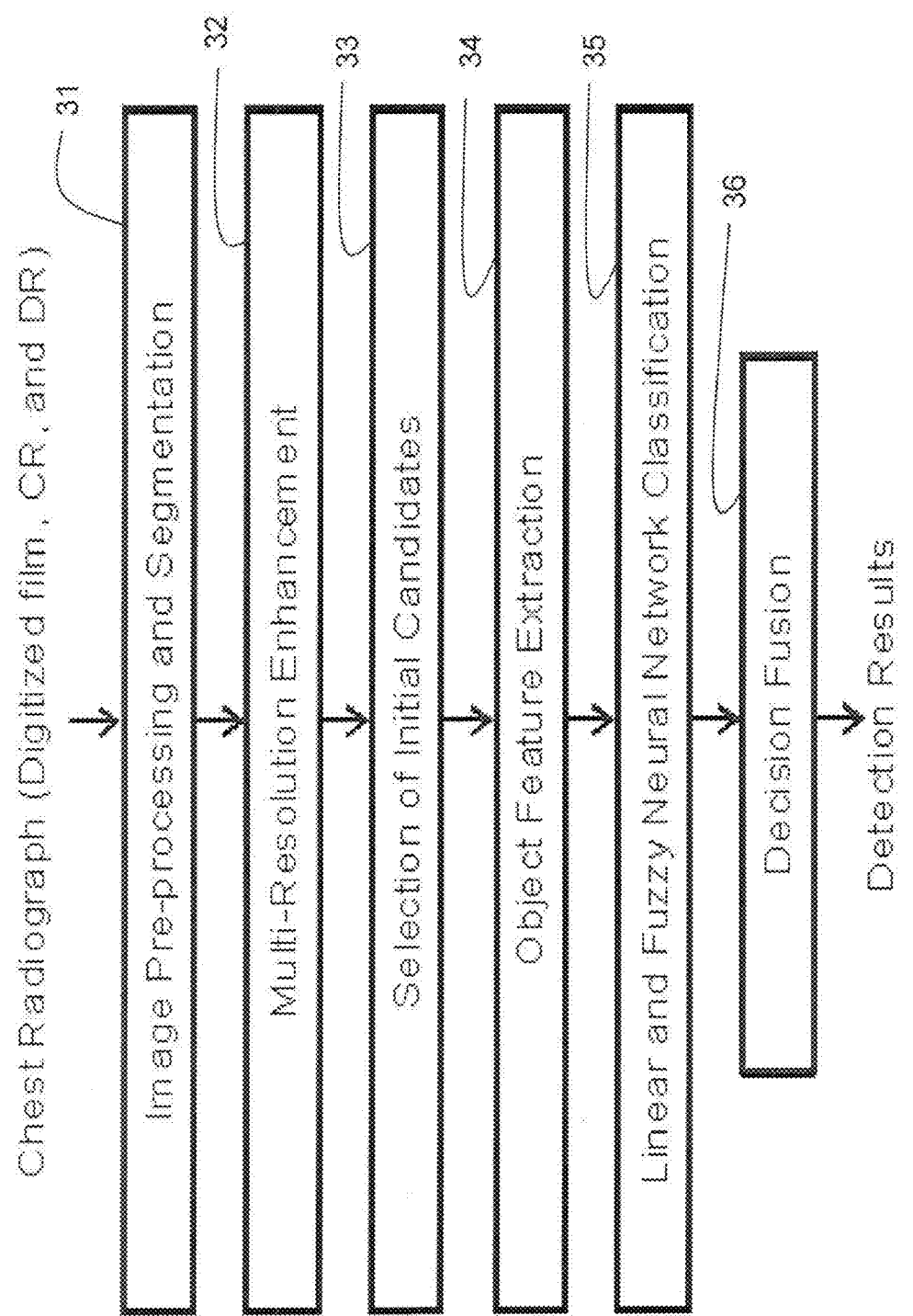
FIG. 3 shows a block diagram of a method and/or system that may be used to implement portions of FIG. 2, according to an embodiment of the invention.

FIG. 3 shows a block diagram/flow diagram of how one or more of modules 21-23 may be implemented, according to various embodiments of the invention. As shown in FIG. 3, a multiple-stage processing scheme may be used in processing the images. Image pre-processing and segmentation 31 is to adjust the contrast of an input digitized image, chest radiograph (CR), and/or digital radiograph (DR) into an image having normalized image contrast. A segmentation algorithm/module in block 31 may be used to delineate lung regions and/or other anatomic regions. Multi-resolution enhancement 32 allows objects of different sizes to be enhanced and matched in an efficient way. Selection of initial candidate abnormalities 33 may he implemented by applying a most-dominant rule and feature to the matched images to select all possible candidates. Object feature extraction 34 may then be used to calculate features of all the candidates associated with shape, growth, edge, contrast of nodules and obvious normal structures. Block 35 may apply neural network-based classification to the results obtained from block 34. Block 35 may include either or both of linear and fuzzy neural network classification. In a particular embodiment, block 35 may employ a linear classifier to eliminate obvious normal candidates based on the linearly discriminated features and a fuzzy neural network classifier to eliminate candidates based on the non-linear properties of candidate features. Decision fusion 36 may then be used to generate optimal detection results from various classifiers based on the performance of each classifier. Exemplary techniques for implementing these blocks may be found, e.g., in U.S. Pat. Nos. 6,795,521, 6,760,468, 6,654,728, and/or 6,549,646, all of which are commonly-assigned and incorporated herein by reference.

The exemplary embodiment of FIG. 2, following processing in blocks 21-23 to produce respective outputs 24-26, which may, for example, be in the form of images, as shown (or may be in the form of data, for example), performs further decision fusion processing 27 on the outputs 24-26 to produce final detection results 2$, which may be in the form of an image, data, etc. Decision fusion processing 27 may include rib-crossing identification, calcification identification, and/or obscured nodule identification. Decision fusion processing 27 is discussed further below. The results of such processing may then be combined with the results 24-26 of the previous processing stages to eliminate false positives (i.e., incorrectly-identified abnormalities).

For example, in connection with decision fusion processing 27, in processing the soft-tissue equivalent image, rib crossings may be incorrectly identified as candidate abnormalities. By identifying these rib crossings, they may be eliminated from the final results 28.

Another example of processing that may be performed in decision fusion processing 27 is to evaluate candidates for being end-on (blood) vessel images in the soft-tissue equivalent image and the standard image. This may be done by computing a contrast-to-radius ratio and checking if there is a fading tubular pattern on the periphery of the candidate abnormality. If the contrast-to-radius ratio is above a predetermined threshold (which, for example, may be set or adjusted by a user or may be determined empirically), the candidate abnormality may be considered to be of low suspicion (and potentially a false positive). Similarly, a fading tubular pattern on the periphery of the candidate abnormality may indicate that the candidate is likely to be a false positive.

Decision fusion processing 27 may include, for example, comparing the results detected from the soft-tissue equivalent image, those detected from the bone equivalent image, and those detected from the standard image. For, the candidate abnormalities in the soft-tissue equivalent image and the bone-equivalent image may be examined for calcification. If calcification is evident, the candidate is more likely to be a true abnormality. This may be based on determining which results include the candidate abnormality. For example, a particular result may be kept (as opposed to being discarded as not being a candidate abnormality) if it appears in the detection output based on the soft-tissue equivalent image but not in the detection output based on the bone equivalent image. A result may also be kept if it appears in all three detection outputs. A detection result may be discarded if it appears in the detection output based on the bone equivalent image but not in the detection output based on the soft-tissue equivalent image and/or in the detection output based on the standard image (this technique may, for example, result in reduction of shadowing due to clavicle bones, which may enhance the detection rate in the apex region of the thorax).

Additionally, block 27 may base its evaluation of candidate nodules located behind the heart region mainly on the detection results based on the standard image.

As discussed above, the results 28 of decision fusion processing 27 may take the form of an image and/or data, for example. In some embodiments of the invention, the results 28 may indicate from which image 14-16 they were obtained; in an image output this may be done by means of different colors, fonts, shapes of markings, labels, etc. Furthermore, an interactive display of a marked image may permit a user to point to and/or click on a mark to display further information regarding a result 28. Such information may include, but is not limited to a result type, a region of interest, and/or one or more quantities indicative of one or more features of the result (e.g., a calcification score computation).

Some embodiments of the invention, as discussed above may he embodied in the form of software instructions on a machine-readable medium. Such an embodiment is illustrated in FIG. 4. The computer system of FIG. 4 may include at least one processor 42, with associated system memory 41, which may store, for example, operating system software and the like. The system may further include additional memory 43, which may for example, include software instructions to perform various applications. The system may also include one or more input/output (I/O) devices 44, for example (but not limited to), keyboard, mouse, trackball, primer, display network connection. etc. The present invention may he embodied as software instructions that may be stored in system memory 41 or in additional memory 43. Such software instructions may also be stored in removable or remote media (for example, but not limited to, compact disks, floppy disks, etc.), which may be read through an I/O device 44 (for example, but not limited to, a floppy disk drive or a network connection used to download the software instructions from a remote location, e.g., a remote storage medium). Furthermore, the software instructions may also be transmitted to the computer system via an I/O device 44, for example, a network connection, in such a case, a signal containing the software instructions may be considered to be a machine-readable medium.

The invention has been described in detail with respect to preferred embodiments, and it will now be apparent from the foregoing to those skilled in the art that changes and modifications may be made without departing from the invention in its broader aspects. The invention, therefore, as defined in the appended claims, is intended to cover all such changes and modifications as fall within the true spirit of the invention.

We claim:

1. A method for performing detection based on radiographic images, the method comprising:
   processing at least a soft-tissue equivalent image derived from at least one radiographic image to detect at least one feature within said at least a soft-tissue equivalent image, wherein said processing includes at least two processes selected from the group consisting of multi-resolution enhancement, object feature extraction, linear neural network classification, and fuzzy neural network classification; and
   performing decision fusion on results obtained using said at least two processes to obtain one or more detection results for said at least one feature.

2. The method according to claim 1, wherein said processing at least one of said derived images further comprises:
   performing image segmentation.

3. The method according to claim 1, wherein said performing decision fusion comprises performing at least one process selected from the group consisting of structure detection; and nodule detection.

4. The method according to claim 1, wherein said performing decision fusion comprises at least one process selected from the group consisting of:

obscured nodule identification; and blood vessel identification.

5. The method according to claim 1, further comprising:

marking said one or more final detection results on a radiographic image.

6. The method according to claim 5, wherein said marking comprises:

using different types of markings to represent different types of findings.

7. The method according to claim 5, wherein a display of said markings enables a user to obtain further information regarding a final detection result associated with a given marking.

8. A machine-readable storage medium containing software code that, upon execution by a processor, causes the processor to implement the method according to claim 1.

9. A system for performing detection based on radiographic images, the method comprising:

at least one processor; and a machine-readable medium containing software code that, when executed by the at least one processor, causes the at least one processor to implement the method according to claim 1.

10. The system according to claim 9, wherein said software code is downloaded from a remote medium to said machine-readable medium.

11. A method for performing detection based on radiographic images, the method comprising:

downloading from a remote medium software code that, when executed by a processor, causes the processor to implement the method according to claim 1; and executing said software code on the processor.

12. A system for performing detection based on radiographic images, the system comprising:

a processing module configured to process at least a soft-tissue equivalent image derived from at least one radiographic image to detect at least one feature within the at least a soft-tissue equivalent image, wherein the processing module is configured to perform at least two processes selected from the group consisting of multi-resolution enhancement, object feature extraction linear neural network classification, and fuzzy neural network classification; and a decision fusion module configured to process results obtained from said at least two processes to obtain one or more detection results for said at least one feature.

13. The method according to claim 12, wherein said decision fusion module is configured to perform at least one process selected from the group consisting of:

obscured nodule identification; and blood vessel identification.

14. A method for performing detection based on radiographic images, the method comprising:

processing at least one radiographic image to obtain one or more derived images including one or more of a soft-tissue equivalent image or a bone equivalent image;

processing at least one of said derived images to detect at least one feature within said at least one derived image, wherein said processing at least one of said derived images comprises at least two processes selected from the group consisting of multi-resolution enhancement, object feature extraction, linear neural network classification, and fuzzy neural network classification; and applying decision fusion to results obtained using the at least two processes.

15. A system for performing detection based on radiographic images, the system comprising:

a first processing module configured to process at least one radiographic image to obtain one or more derived images including one or more of a soft-tissue equivalent image or a bone equivalent image; and a second processing module configured to process at least one of said derived images to detect at least one feature within said at least one derived image, wherein the second processing module is configured to perform at least two processes selected from the group consisting of multi-resolution enhancement, object feature extraction, linear neural network classification, and fuzzy neural network classification and to perform decision fusion on results obtained using said at least two processes.

* * * * *